US008016768B2

(12) United States Patent
Lau et al.

(10) Patent No.: US 8,016,768 B2
(45) Date of Patent: Sep. 13, 2011

(54) HAND SENSORY ASSESSMENT DEVICE

(75) Inventors: Kin-tak Lau, Kowloon (HK); Mei-ling Lau, Kowloon (HK); Chetwyn Chan, Kowloon (HK)

(73) Assignee: The Hong Kong Polytechnic University, Hong Kong (CN)

( * ) Notice: Subject to any disclaimer, the term of this patent is extended or adjusted under 35 U.S.C. 154(b) by 18 days.

(21) Appl. No.: 12/222,827

(22) Filed: Aug. 18, 2008

(65) Prior Publication Data

US 2010/0106050 A1 Apr. 29, 2010

(51) Int. Cl.
*A61B 19/00* (2006.01)
*A61B 5/103* (2006.01)
*A61B 5/117* (2006.01)

(52) U.S. Cl. ......................... 600/557; 600/587; 600/553

(58) Field of Classification Search .................. 600/557, 600/552–555, 587, 595, 372, 382, 384, 386, 600/388, 390, 393; 73/379.01–379.09
See application file for complete search history.

(56) References Cited

U.S. PATENT DOCUMENTS

| | | | | |
|---|---|---|---|---|
| 5,027,828 | A * | 7/1991 | Kovacevic et al. | 600/587 |
| 6,387,055 | B1 | 5/2002 | Christy | |
| 6,679,857 | B1 | 1/2004 | Bastia et al. | |
| 6,702,756 | B2 | 3/2004 | Brown | |
| 6,847,846 | B2 * | 1/2005 | Sun | 607/46 |
| 2004/0189606 | A1 * | 9/2004 | Powpong | 345/163 |

* cited by examiner

*Primary Examiner* — Jeffrey G Hoekstra
(74) *Attorney, Agent, or Firm* — George G. Wang; Wilkinson & Grist

(57) ABSTRACT

The present invention relates to a hand sensory assessment device capable of point localization, two-point discrimination, vibration, and texture discrimination for assessing and training patients. The device possesses multiples of pins serving as contacting points that are capable of treating multiples points on a patients hand.

4 Claims, 4 Drawing Sheets

HAND SENSORY ASSESSMENT DEVICE

BACKGROUND

A stroke is defined as the rapid developed of facial or global disturbance of cerebral function, lasting more than 24 hours or leading to death, with no apparent cause other than of vascular origin. Following stroke, 40% of patients remain permanently disabled and dependent on assistance. However, recovery is usually greater if it occurs earlier. The majority of strokes affect the upper limb more than the lower limb, and patients with a severely paralyzed hand at the outset have both a high risk for mortality and little hope regaining a useful hand.

Sensory re-education (SRE) is a process in which the patient learns with the therapists to discover and use whatever sensations are available to him and in whatever reduced or distorted from they may "filter through". SRE is a collaborative activity, involving mutual sharing of knowledge and the sharing of control and responsibility. SRE begins with the patient and the therapist discussing treatment together, and the patient trying it out with his good hand.

A number of different methods are utilized to perform SRE for hands. A Pellenberg box provides a method of teaching shape discrimination; object recognition allows comparison of rough and smooth surfaces by touch. U.S. Pat. No. 6,387,055 teaches a hand-held discrimination designed to test nerve sensory functions. U.S. Pat. No. 6,702,756 teaches methods of diagnosing neurological impairments and apparatuses. One apparatus embodiment incorporates tactile stimulators for contacting the hands of patients. The apparatus has as a weakness its ability to engage the user's hand in two locations at one time. Other locations can be contacted, but this requires the patient to move their hand; this is particularly difficult for stroke sufferers with plegic arm.

It is an object of the present invention to overcome the disadvantages and problems in the prior art.

DESCRIPTION

The present invention relates to a hand sensory assessment device capable of point localization, two-point discrimination, vibration, and texture discrimination for assessing and training patients. The device, as a contacting agent, possesses multiples of pins serving as contacting points that are capable of treating multiples points on a patients hand.

These and other features, aspects, and advantages of the apparatus and methods of the present invention will become better understood from the following description, appended claims, and accompanying drawings where:

The following description of certain exemplary embodiment(s) is merely exemplary in nature and is in no way intended to limit the invention, its application, or uses.

Figure 1:
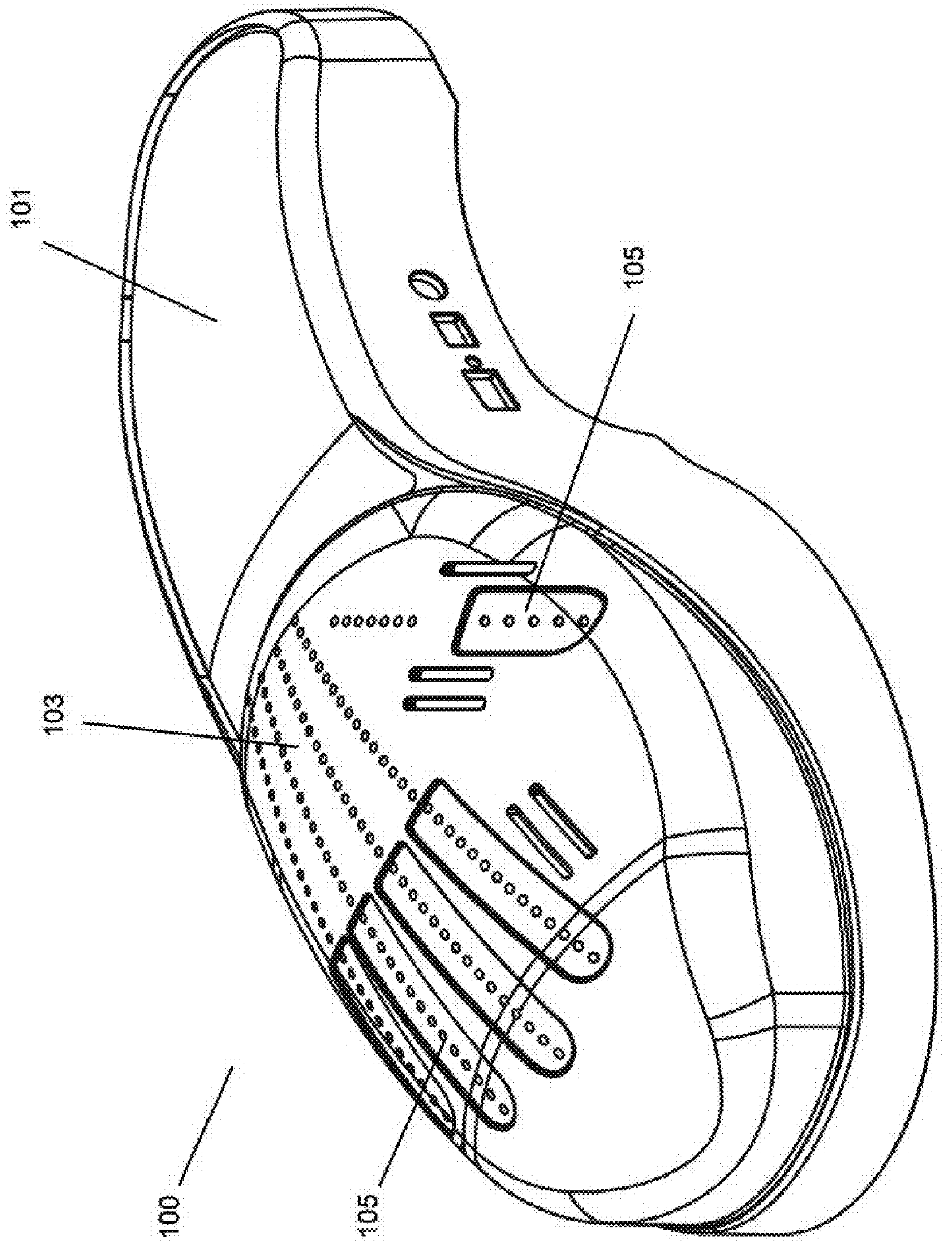
FIG. 1 shows the hand sensory device of the present invention.

Now, to FIGS. 1-4,

FIG. 1 is an embodiment of a hand sensory assessment device 100. The device 100 includes a housing 101, pin contact holes 103, and straps 105.

The pin contact holes 103 allow pins positioned underneath the housing 101 to rise and fall in order to engage the hand positioned on the device 100. The number of pin contact holes 103 is equal to the number of pins.

Straps 105 are used to keep the hand securely attached to the device 100.

Figure 2:
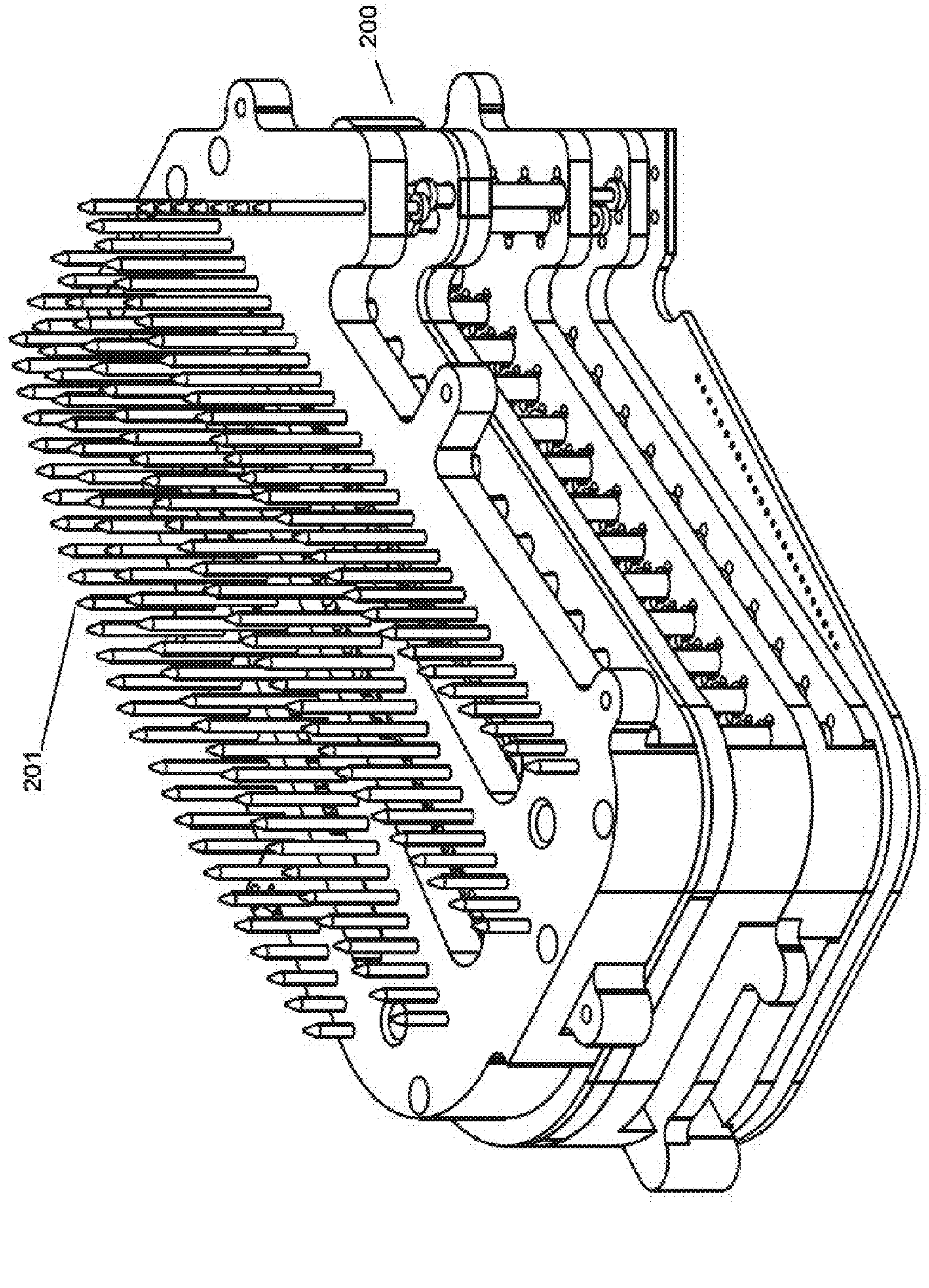
FIG. 2 shows the present device, minus the housing.

FIG. 2 shows the present device 200 minus the housing. As shown, the device 200 is comprised of multiples of pin-solenoid units 201 each comprising a pin and a solenoid. The pin-solenoid unit 201 can number from between 100 to 150 units. In one embodiment, 130 pin-solenoid units 201 are positioned in the device 200. The device 200 further includes circuit boards for conducting electricity through the device 200, and a microcontroller (not shown). The microcontroller is suitable for controlling the solenoids of the pin-solenoid units 201, as well as controlling the overall choreography by which the solenoids of the pin-solenoid units fire during a treatment session. The microcontroller possess code stored thereon to allow manipulation of the solenoids, and correspondingly the pins, and to accept further choreographed pin movement.

In use, the patient's hand is positioned palm down on the device. Upon activation, the device will deliver a choreographed treatment pattern in which the pins engage various points on the palm on the patient. Each time, a designated pin which was preset by the program will generate push up and drop down motions based on the instructions given by the solenoid (which, in turn, is controlled by the microcontroller). The device thus involves the conversion of electrical signals to mechanical movements in the treatment of patients.

The device is also capable of testing by vibration motion, whereby the patient will be gauged as to whether they can feel vibration motion taken on their palm. The concept of movement stimulates the motion of therapists who manually pin the patients palm and fingers by blunt probe or with a tuning fork. The device provides a standard assessing pattern as well as identical assessments to be conducted repeatedly.

The device is further suitable for carrying out texture discrimination function. This is accomplished by utilizing a roller with an attached spatial pattern into a coated ABS housing, a curved shaped with silicon platform whereby the patient can rest her wrist so as to alleviate stress during assessment process. The patient is requested to define which two patterns are the same when they touch on it.

Figure 3:
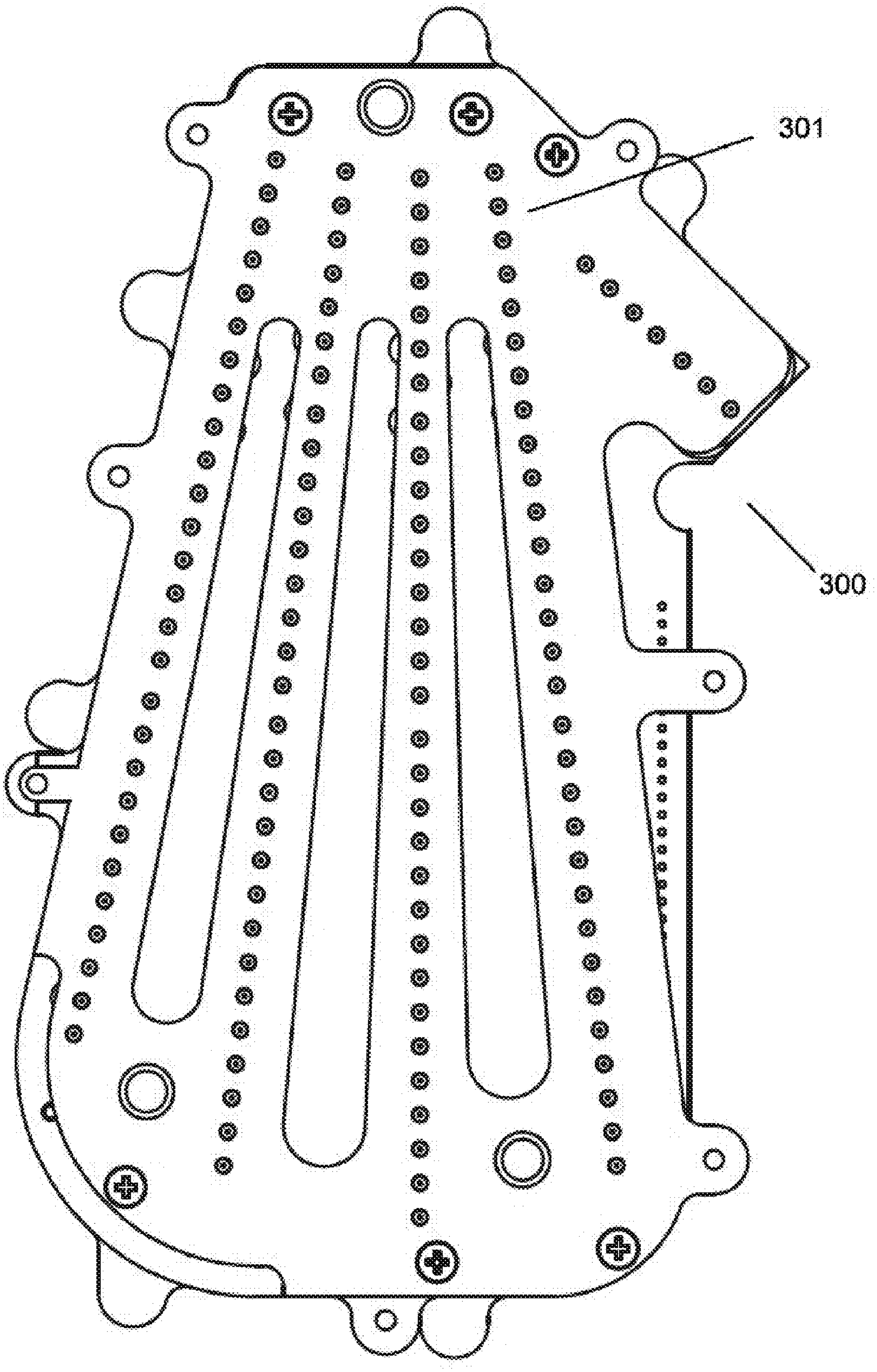
FIG. 3 is a top-side view of the present device, minus the housing.

FIG. 3 shows an embodiment of the present device 300, specifically a right-handed embodiment. As shown, the pins are arranged to contract a user's hand in a variety of positions.

Figure 4:
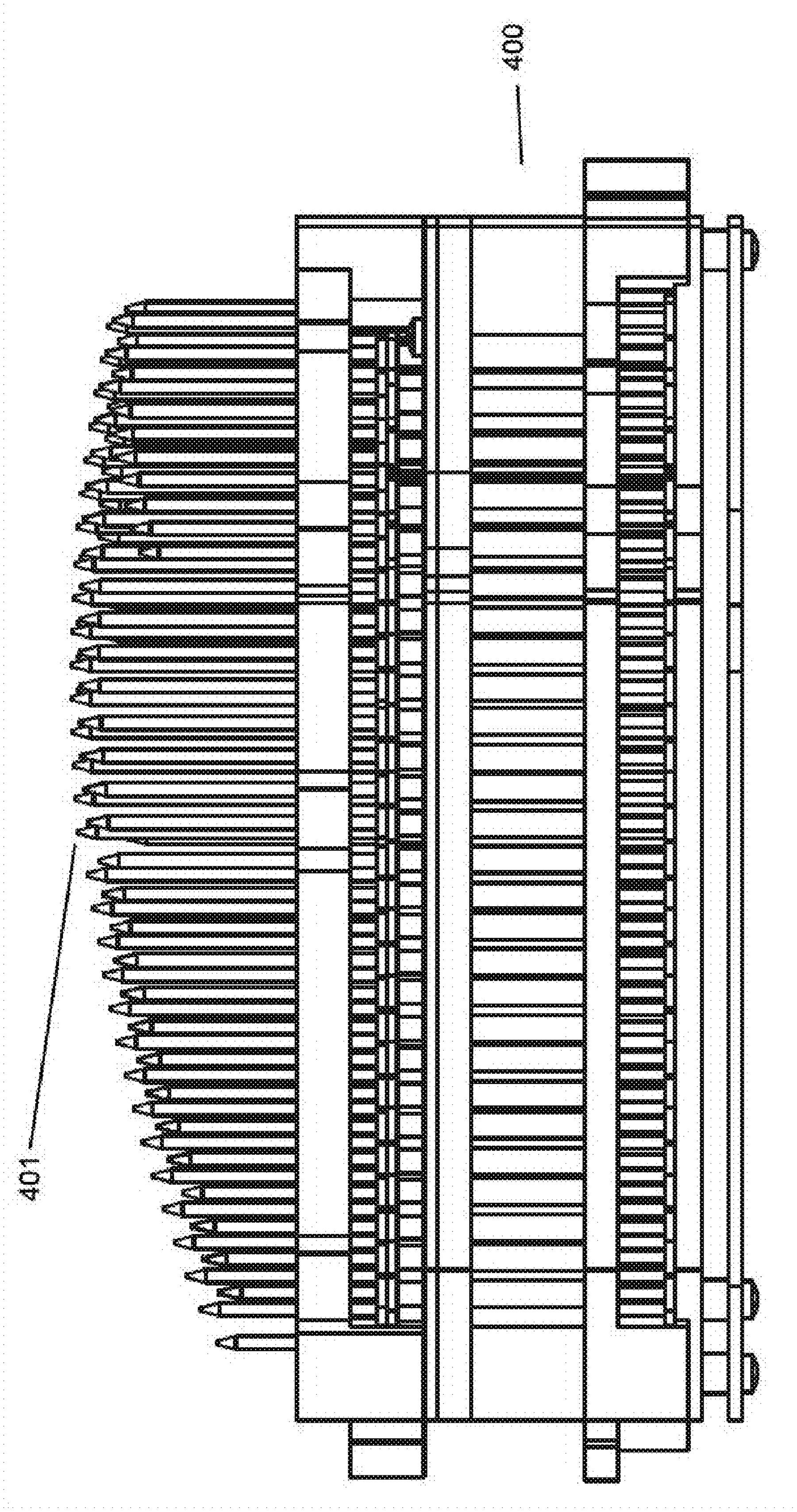
FIG. 4 is a side view of the present device, minus the housing.

FIG. 4 shows a side view of the present device 400. In this embodiment, the housing has been removed to show the pins 401 that contact the hand.

Having described embodiments of the present system with reference to the accompanying drawings, it is to be understood that the present system is not limited to the precise embodiments, and that various changes and modifications may be effected therein by one having ordinary skill in the art without departing from the scope or spirit as defined in the appended claims.

In interpreting the appended claims, it should be understood that:

a) the word "comprising" does not exclude the presence of other elements or acts than those listed in the given claim;

b) the word "a" or "an" preceding an element does not exclude the presence of a plurality of such elements;

c) any reference signs in the claims do not limit their scope;

d) any of the disclosed devices or portions thereof may be combined together or separated into further portions unless specifically stated otherwise; and e) no specific sequence of acts or steps is intended to be required unless specifically indicated.

The invention claimed is:

1. A hand sensory assessment device for assessing and training stroke sufferers, comprising a housing and a pin assembly; said housing covering said pin assembly, comprising (a) a surface capable of accommodating an entire palm of a patient resting thereon in a palm down position, (b) a hand strap and a thumb strap for securing said palm on said surface of said housing, and (c) at least 100 pin holes disposed through said surface; and said pin assembly being positioned inside said housing and beneath said surface of said housing and comprising at least 100 pin-solenoid units which are aligned with said pin holes in said surface of said housing and capable of pushing up and dropping motions through said pins holes of said surface, wherein said pin-solenoid units are each programmed to participate in an overall choreography program in which electric signals are converted into mechanical movements of pins in a choreographed manner.

2. The hand sensory assessment device for assessing and training stroke sufferers in claim 1, wherein said pin assembly comprises 130 pin-solenoid units each of which is in connection with a microcontroller for receiving electronic signals therefrom.

3. The hand sensory assessment device for assessing and training stroke sufferers in claim 1, wherein said pin-solenoid units are positioned in a plurality of lines.

4. The hand sensory assessment device for assessing and training stroke sufferers in claim 3, wherein said pin-solenoid units are positioned in five lines, aligned with five fingers of said entire palm of a patient resting thereon in a palm-down position.

* * * * *